(12) United States Patent
Costigan et al.

(10) Patent No.: US 9,584,730 B2
(45) Date of Patent: Feb. 28, 2017

(54) APPARATUS, SYSTEMS, AND METHODS FOR A MULTI-POSITION IMAGE SENSOR

(71) Applicant: Cognex Corporation, Natick, MA (US)

(72) Inventors: George Costigan, Tyngsboro, MA (US); Laurens Nunnink, Eindhoven (NL); Aaron Wallack, Natick, MA (US); Roger Sumner, Natick, MA (US)

(73) Assignee: COGNEX CORPORATION, Natick, MA (US)

( * ) Notice: Subject to any disclaimer, the term of this patent is extended or adjusted under 35 U.S.C. 154(b) by 286 days.

(21) Appl. No.: 14/171,251

(22) Filed: Feb. 3, 2014

(65) Prior Publication Data
US 2015/0222820 A1   Aug. 6, 2015

(51) Int. Cl.
*H04N 3/14* (2006.01)
*H04N 5/232* (2006.01)
(Continued)

(52) U.S. Cl.
CPC ....... *H04N 5/23296* (2013.01); *G01M 17/027* (2013.01); *G01N 21/8806* (2013.01);
(Continued)

(58) Field of Classification Search
CPC .......... A61B 8/06; A61B 8/465; A61B 8/468; A61B 8/469; A61B 8/488; A61B 8/5223; A61B 8/5292; G01B 11/24; G01M 17/027; G01N 2021/95638; G01N 21/8806; G02B 7/28; G06K 9/0014; G06T 2207/10132; G06T 2207/30104; G06T 7/0081; H04N 3/155; H04N 3/1562;H04N 5/2252; H04N 5/2253; H04N 5/23296; H04N 5/335; Y10T 29/49002
(Continued)

(56) References Cited

U.S. PATENT DOCUMENTS 6,249,341 B1* 6/2001 Basiji .................... G01J 3/2803
                                                         356/318
6,583,865 B2* 6/2003 Basiji ........................ G01J 3/02
                                                          356/73
(Continued)

OTHER PUBLICATIONS

Merklinger, H.M., "The Scheimpflug Principle—Part I," Shutterbug, 2 pgs., Nov. 1992.
(Continued)

*Primary Examiner* — Shan Elahi
(74) *Attorney, Agent, or Firm* — Wilmer Cutler Pickering Hale and Dorr LLP

(57) ABSTRACT

The disclosed apparatus, systems, and methods provide for a displacement sensor with a multi-position image sensor. The displacement sensor includes an optical lens. The displacement sensor includes an image sensor configured to view an object through the lens along a plane of focus that is not parallel to an image plane of the image sensor. The displacement sensor includes a laser for illuminating the object by the displacement sensor, wherein the laser is: spaced from the lens at a fixed distance, and configured to project a line of light along the plane of focus of the image sensor. The displacement sensor comprises a first configuration wherein the image sensor is at a first location along an image plane with a first field of view along the plane of focus, and a second configuration at a second location with a different field of view.

20 Claims, 15 Drawing Sheets

(51) Int. Cl.
*H04N 5/225* (2006.01)
*H04N 5/335* (2011.01)
*G01M 17/02* (2006.01)
*G01N 21/88* (2006.01)
*G02B 7/28* (2006.01)
*G01N 21/956* (2006.01)
*G01B 11/24* (2006.01)

(52) U.S. Cl.
CPC ............... *G02B 7/28* (2013.01); *H04N 3/155* (2013.01); *H04N 3/1562* (2013.01); *H04N 5/2252* (2013.01); *H04N 5/2253* (2013.01); *H04N 5/335* (2013.01); *G01B 11/24* (2013.01); *G01N 2021/95638* (2013.01); *Y10T 29/49002* (2015.01)

(58) Field of Classification Search
USPC ........................................................ 348/142
See application file for complete search history.

(56) References Cited

U.S. PATENT DOCUMENTS

| | | | | |
|---|---|---|---|---|
| 6,700,617 | B1* | 3/2004 | Hamamura | H04N 5/2254 348/340 |
| 7,330,784 | B2* | 2/2008 | Johnson | B60N 2/002 280/731 |
| 7,889,263 | B2* | 2/2011 | Ortyn | C12Q 1/6816 348/335 |
| 8,009,189 | B2* | 8/2011 | Ortyn | G01N 21/6458 348/80 |
| 8,451,524 | B2* | 5/2013 | Ortyn | G02B 26/0858 356/338 |
| 2006/0208169 | A1* | 9/2006 | Breed | B60N 2/002 250/221 |
| 2006/0217864 | A1* | 9/2006 | Johnson | B60N 2/002 701/45 |
| 2006/0229744 | A1* | 10/2006 | Patzwald | G01B 11/162 700/59 |
| 2008/0059069 | A1* | 3/2008 | Trutna | G08G 1/166 701/301 |
| 2008/0292146 | A1* | 11/2008 | Breed | B60N 2/002 382/118 |
| 2009/0262363 | A1* | 10/2009 | Keshavmurthy | G01B 11/2509 356/511 |
| 2009/0321399 | A1* | 12/2009 | Inagawa | B23K 26/0673 219/121.69 |
| 2010/0040355 | A1* | 2/2010 | Craen | G03B 13/32 396/90 |
| 2012/0050750 | A1* | 3/2012 | Hays | G01J 9/04 356/519 |
| 2012/0218172 | A1* | 8/2012 | Border | G02B 27/0093 345/8 |
| 2012/0274937 | A1* | 11/2012 | Hays | G01S 17/58 356/337 |
| 2013/0089183 | A1* | 4/2013 | Sura | A61B 6/4225 378/98.2 |
| 2013/0127980 | A1* | 5/2013 | Haddick | G06F 3/013 348/14.08 |
| 2013/0201316 | A1* | 8/2013 | Binder | H04L 67/12 348/77 |
| 2014/0002608 | A1* | 1/2014 | Atwell | G01B 5/008 348/46 |
| 2015/0116413 | A1* | 4/2015 | Duke | B41J 29/393 347/19 |

OTHER PUBLICATIONS

Merklinger, H.M., "View Camera Focus and Depth of Field—Part I," View Camera, 4 pgs., Jul./Aug. 1996.

* cited by examiner

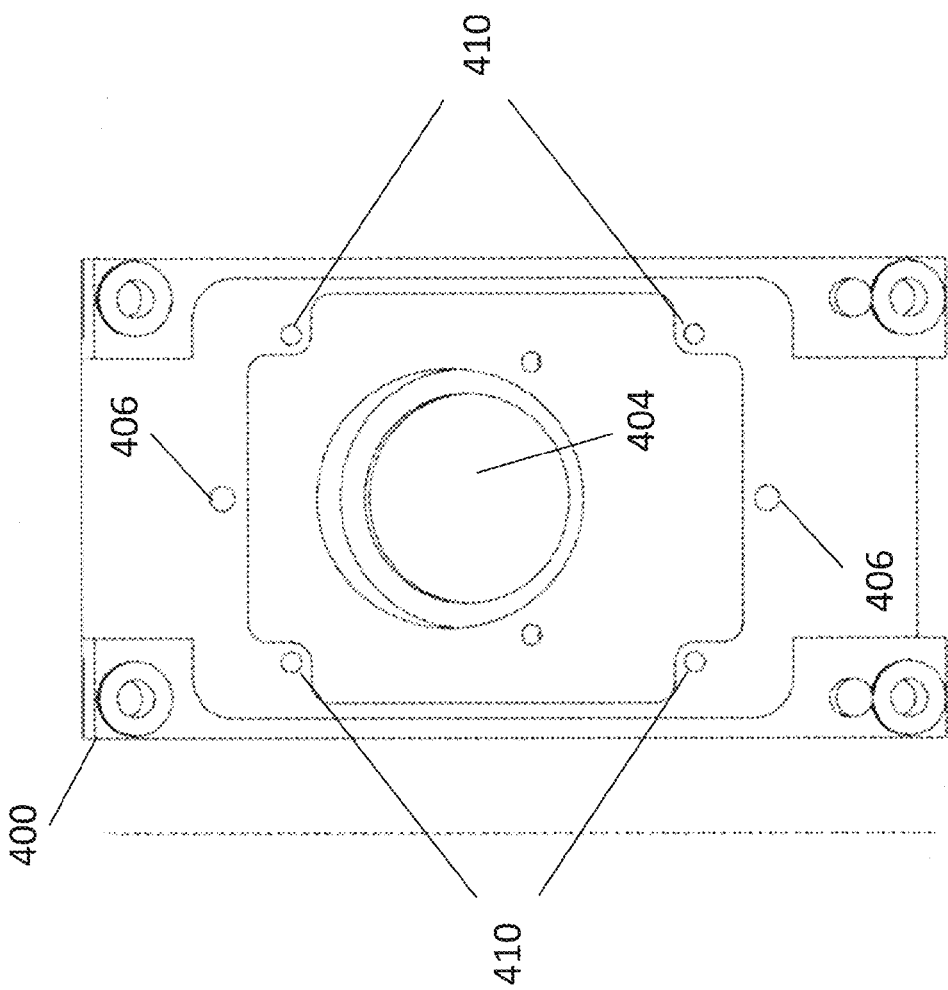

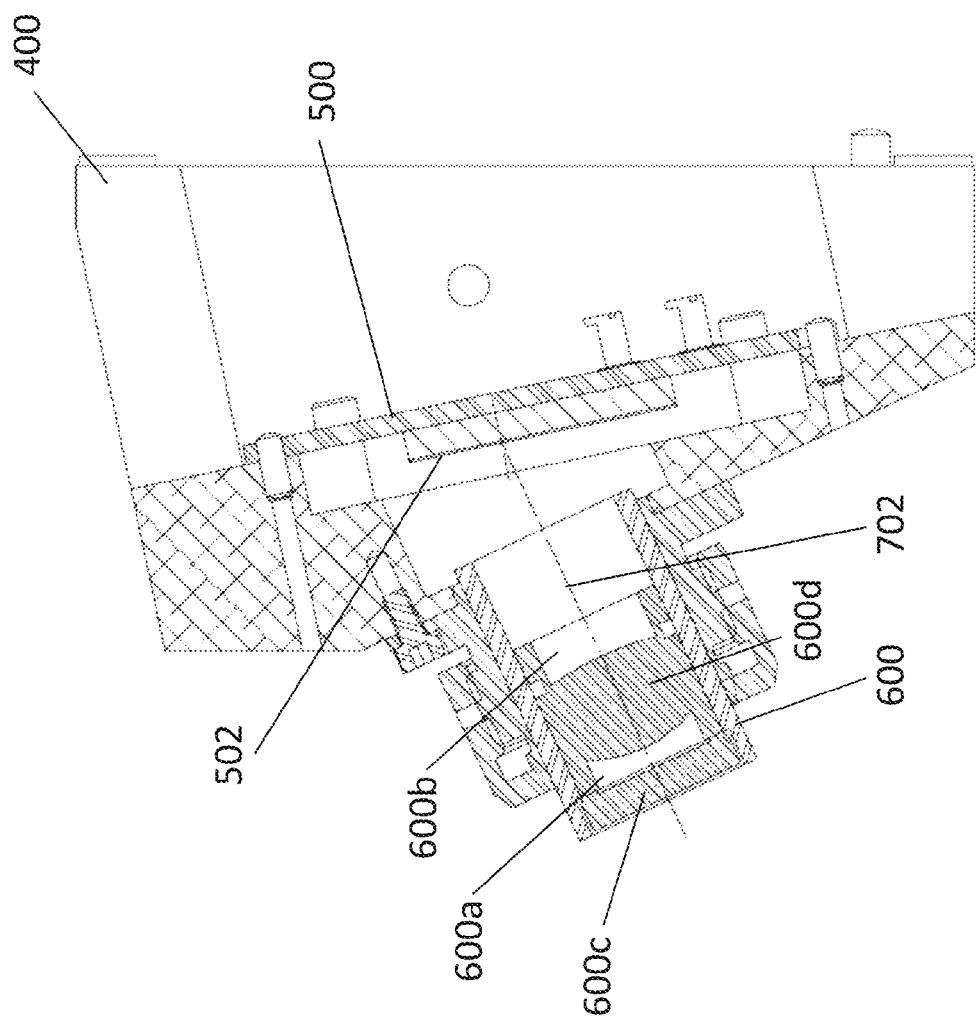

APPARATUS, SYSTEMS, AND METHODS FOR A MULTI-POSITION IMAGE SENSOR

TECHNICAL FIELD

The disclosed computerized systems, apparatus, and computerized methods generally relate to a multi-position image sensor, and in particular a multi-position image sensor for achieving multiple fields of view.

BACKGROUND

Machine vision tools can be used to automate the inspection of parts of different sizes and shapes (e.g., during manufacturing processes). Displacement sensors, for instance, can be used to measure the displacement of an object from a plane of reference, such as while the object travels along a platform or conveyor belt, to measure the three dimensional displacement of the object. These and other machine vision techniques often require using different optics depending on the particular application, such as the size or shape of the feature being measured, or the amount of resolution required for the particular application. For example, if an image sensor is being used to inspect a small feature of an object (e.g., a corner of a microchip), then the image sensor may be configured with a small field of view ("FOV") to inspect the feature since it is relatively small and requires a high amount of resolution. If the image sensor is instead being used to inspect a larger object or a larger feature of an object (e.g., tire treads), then the image sensor may be configured with a larger FOV to inspect the larger feature (which may in-turn sacrifice resolution), because otherwise the image sensor may not be able to inspect the entire feature. The displacement sensor's measured height values form a 2D profile of the object in the FOV.

While it can be desirable to use a single sensor for different applications, it is often difficult to change the configuration of the image sensor to achieve multiple (or different) FOVs without changing other aspects of the sensor. For example, adjusting the FOV often requires adjusting parameters in the optical setup of the sensor, such as the distance between the image sensor and the lens of the sensor, the focal length of the lens, the angle between lens, sensor and/or plane of focus, and/or other parameters. Therefore sensors are usually designed and built such that they are configured for only one application (e.g., they can only achieve one FOV). However, changing between different image sensor housings to adapt a system to different imaging scenarios can increase manufacturing costs since different housings need to be machined, and can add complexities to managing machine vision applications for different products.

SUMMARY

In accordance with the disclosed subject matter, apparatus, systems, non-transitory computer-readable media, and computerized methods are provided for adjusting the field of view of a sensor (e.g., a displacement sensor) without needing to change the mechanical housing of the sensor.

Some embodiments include a displacement sensor for determining characteristics of an object. The displacement sensor includes an optical lens. The displacement sensor includes an image sensor configured to view an object through the lens along a plane of focus that is not parallel to an image plane of the image sensor. The displacement sensor includes a laser for illuminating the object by the displacement sensor, wherein the laser is spaced from the lens at a fixed distance, and configured to project a line of light along the plane of focus of the image sensor. The displacement sensor includes a first configuration wherein the image sensor is at a first location along an image plane of the image sensor in the displacement sensor, such that the image sensor has a first field of view along the plane of focus, and a second configuration wherein the image sensor is at a second location along the image plane of the image sensor in the displacement sensor, such that the image sensor has a second field of view along the plane of focus that is wider than the first field of view.

Some embodiments include a displacement sensor for determining characteristics of an object. The displacement sensor includes an optical lens. The displacement sensor includes an image sensor configured to view an object through the lens along a plane of focus that is not parallel to an image plane of the image sensor. The displacement sensor includes a laser for illuminating the object by the displacement sensor, wherein the laser is spaced from the lens at a fixed distance, and configured to project a line of light along the plane of focus of the image sensor. The displacement sensor is adjustable to achieve a first configuration wherein the image sensor is at a first location along an image plane of the image sensor in the displacement sensor, such that the image sensor has a first field of view along the plane of focus, and a second configuration wherein the image sensor is at a second location along the image plane of the image sensor in the displacement sensor, such that the image sensor has a second field of view along the plane of focus that is wider than the first field of view.

Some embodiments include a method of manufacturing a displacement sensor. The method includes mounting an optical lens to a displacement sensor housing. The method includes mounting an image sensor to the displacement sensor housing, wherein the image sensor is configured to view an object through the lens along a plane of focus that is not parallel to an image plane of the image sensor, and wherein the displacement sensor is mounted in one of a plurality of configurations, including a first configuration wherein the image sensor is at a first location along an image plane of the image sensor in the displacement sensor, such that the image sensor has a first field of view along the plane of focus, and a second configuration wherein the image sensor is at a second location along the image plane of the image sensor in the displacement sensor, such that the image sensor has a second field of view along the plane of focus that is wider than the first field of view. The method includes mounting a laser for illuminating the object by the displacement sensor on the displacement sensor housing, wherein the laser is spaced from the lens at a fixed distance, and configured to project a line of light along the plane of focus of the image sensor.

The disclosed apparatus, systems, and methods, described herein can provide techniques for adjusting the field of view of an image sensor configured to capture light projected by a laser. Displacement sensors, for instance, are often configured to view a laser line at an angle to be able to measure displacement of the object. The techniques disclosed herein can be used to adjust the field of view of the displacement sensor along a plane of focus that corresponds with the projected laser line. The techniques can allow adjustment of the field of view without needing to change a pre-configured distance between the laser and the lens.

There has thus been outlined, rather broadly, the features of the disclosed subject matter in order that the detailed description thereof that follows may be better understood, and in order that the present contribution to the art may be better appreciated. There are, of course, additional features of the disclosed subject matter that will be described hereinafter and which will form the subject matter of the claims appended hereto. It is to be understood that the phraseology and terminology employed herein are for the purpose of description and should not be regarded as limiting.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 4C illustrates a bottom perspective view of a housing configurable for different PCB mounting locations, in accordance with some embodiments.

FIG. 7A illustrates a side perspective view of the lens and the PCB with the image plane sensor mounted within the housing at a nominal position, in accordance with some embodiments.

DETAILED DESCRIPTION

In the following description, numerous specific details are set forth regarding the systems and methods of the disclosed subject matter and the environment in which such systems and methods may operate, etc., in order to provide a thorough understanding of the disclosed subject matter. It will be apparent to one skilled in the art, however, that the disclosed subject matter may be practiced without such specific details, and that certain features, which are well known in the art, are not described in detail in order to avoid complication of the disclosed subject matter. In addition, it will be understood that the examples provided below are exemplary, and that it is contemplated that there are other systems and methods that are within the scope of the disclosed subject matter.

The techniques disclosed herein provide for a sensor (e.g., a displacement sensor) with an optical lens and an image sensor configured to view an object through the lens. The optical configuration of the image sensor and laser, which projects a line of light along the plane of focus (referred to herein as the "PoF"), can be configured such that the PoF is not parallel to the image plane of the image sensor (e.g., as defined by the Scheimpflug principle). The image sensor can include a laser for illuminating the object being viewed, which is spaced from the lens at a fixed distance (e.g., manufactured in a housing with such a configuration). The laser can be configured to project light along the plane of focus of the image sensor, such that the image sensor views the light projected by the laser at an angle. The image sensor can be adjustable within the housing of the sensor to move the field of view (referred to herein as "FOV") along the plane of focus. The sensor can have different configurations where the image sensor can be moved to different locations along the image plane of the image sensor (e.g., along an axis) to change the field of view of the image sensor along the plane of focus.

In some embodiments, the techniques include translating the image sensor along the axis of the Scheimpflug plane while maintaining the baseline distance between the laser and the imaging lens (e.g., as installed within the sensor housing). Depending on the direction of the shift related to the optics of the system, the field of view will either increase or decrease. If the translation of the image sensor can be accommodated within the framework of the mechanical housing, then it is not necessary to change the baseline distance between the lens and the laser, or to replace the mechanical housing to adapt the displacement sensor to different applications.

Figure 1A:
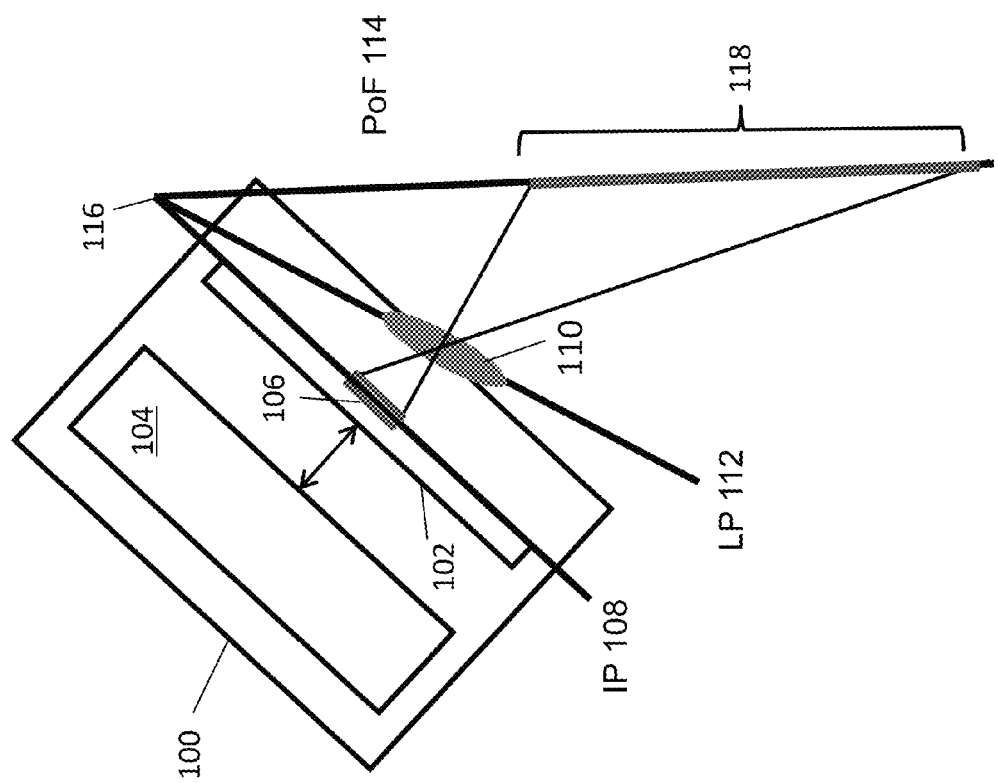
FIG. 1A illustrates an exemplary displacement sensor in accordance with some embodiments.

FIG. 1A illustrates an exemplary displacement sensor 100 in accordance with some embodiments. The displacement sensor 100 includes a motion stage 102 and a controller 104. Image sensor 106 is mounted to the motion stage 102. The controller 104 is configured to control the motion stage 102 to move the location of the image sensor 106 along the image plane 108. The apparatus 100 includes a lens 110 that defines the lens plane 112. The angle between the lens plane 112 and the image plane 108 and the location of the image sensor 106 along the motion stage 102 with respect to the optical axis of the lens 110 (not shown) results in the plane of focus (PoF) 114, such that the image sensor 106 has a field of view ("FOV") 118 along the PoF.

As shown in the embodiment of FIG. 1A, since the image plane 108 is not parallel to the lens plane 112, the displacement sensor 100 can focus on the PoF 114 even though the PoF 114 is not parallel to the image plane. This configuration is different than other imaging systems such as those in which the image plane is parallel to the lens plane, which results in the PoF also being parallel to the image and lens planes.

The displacement sensor 100 can be used in various types of applications. The displacement sensor 100 can be used to inspect small objects, such as components of a PCB. For example, the displacement sensor 100 can inspect portions of a PCB to make sure they meet the relevant specifications (e.g., such as measure the length of connector pins on a PCB to ensure that the pins all have the same height). As another example, the displacement sensor can be used to measure the three-dimensional shape of objects on an assembly line. For example, the displacement sensor 100 can be used to measure objects as they are manufactured (e.g., to ensure the objects maintain a consistent shape, or to make sure the objects are the proper size for product packaging). The displacement sensor can also be used to inspect larger objects, such as verifying the lettering on a side wall of a tire, or measuring the treads of a tire.

Figure 1B:
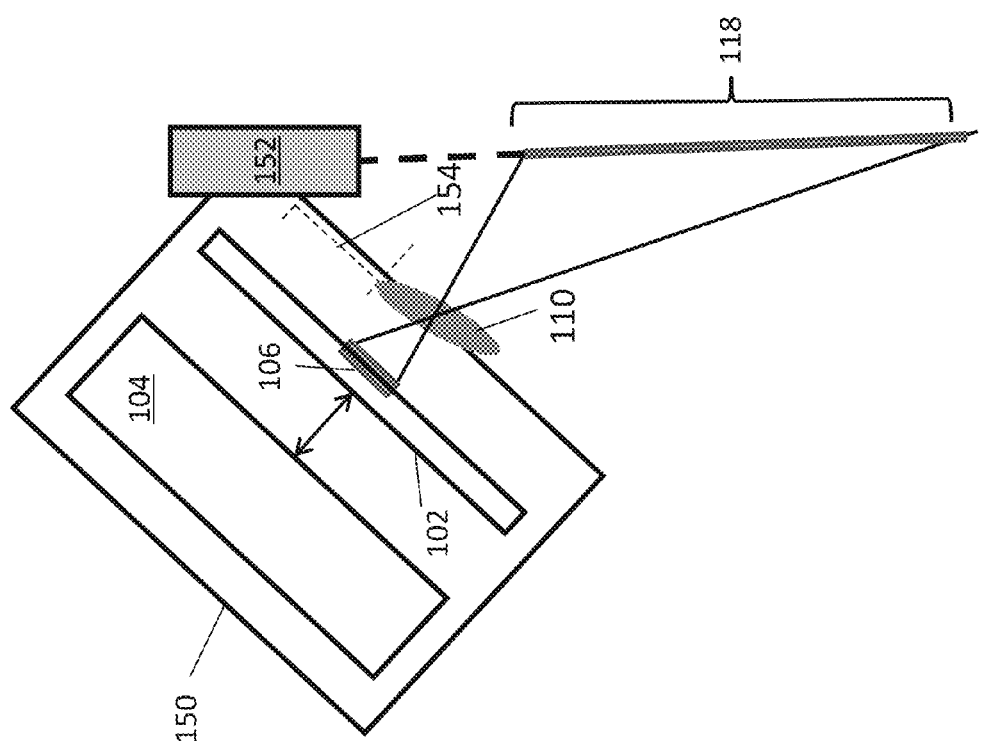
FIG. 1B illustrates a laser-based displacement sensor in accordance with some embodiments.

In some embodiments, the displacement sensor 100 can be a laser-based system, where the image sensor 106 is configured to capture illumination projected by the laser (e.g., projected onto an object). FIG. 1B illustrates a laser-based displacement sensor 150 in accordance with some embodiments. The laser-based displacement sensor 150 includes the motion stage 102, the controller 104, the image sensor 106, and the lens 110 from FIG. 1A, and also includes a laser 152. The distance 154 between the laser 152 and the lens 110 is often referred to as the baseline between the laser 152 and the lens 110.

Referring to FIGS. 1A and 1B, the displacement sensor 100 (e.g., via the controller 104) can be configured to control the position of the image sensor 106 so that the POV of the image sensor 106 is aligned with a target area that is illuminated by the laser 152. The motion stage 102 can be, for example, a single axis motion stage that is configured to move along a particular direction (or axis). The controller 104 can control the motion stage to move the location of the motion stage 102 along the axis (and therefore the location of the image sensor 106) to shift the POV 118 of the image sensor 106 along the PoF 114, such as described with reference to FIGS. 3A and 3B. The baseline between the image sensor 106 and the laser 152 can be maintained while providing both near-field and far-field capabilities by moving the location of the image sensor 106, as will be explained in further detail below.

As shown in FIG. 1A, the image plane 108, lens plane 112 and PoF 114 intersect at a line 116. A principle referred to as the Scheimpflug principle is a geometric rule that describes the orientation of the plane of focus of an optical system (e.g., such as the displacement sensor 100) when the lens plane is not parallel to the image plane. As explained by the Scheimpflug principle, when the lens and image planes are not parallel (e.g., as illustrated in FIG. 1A), adjusting the focus by moving the image sensor closer to (or further away from) the lens 110 rotates the PoF rather than displacing it along the lens axis. One of skill can appreciate that while the techniques described herein use the Scheimpflug principle, other optical principles can be used to achieve the same effect (e.g., placing a prism in the optical path).

Figure 1C:
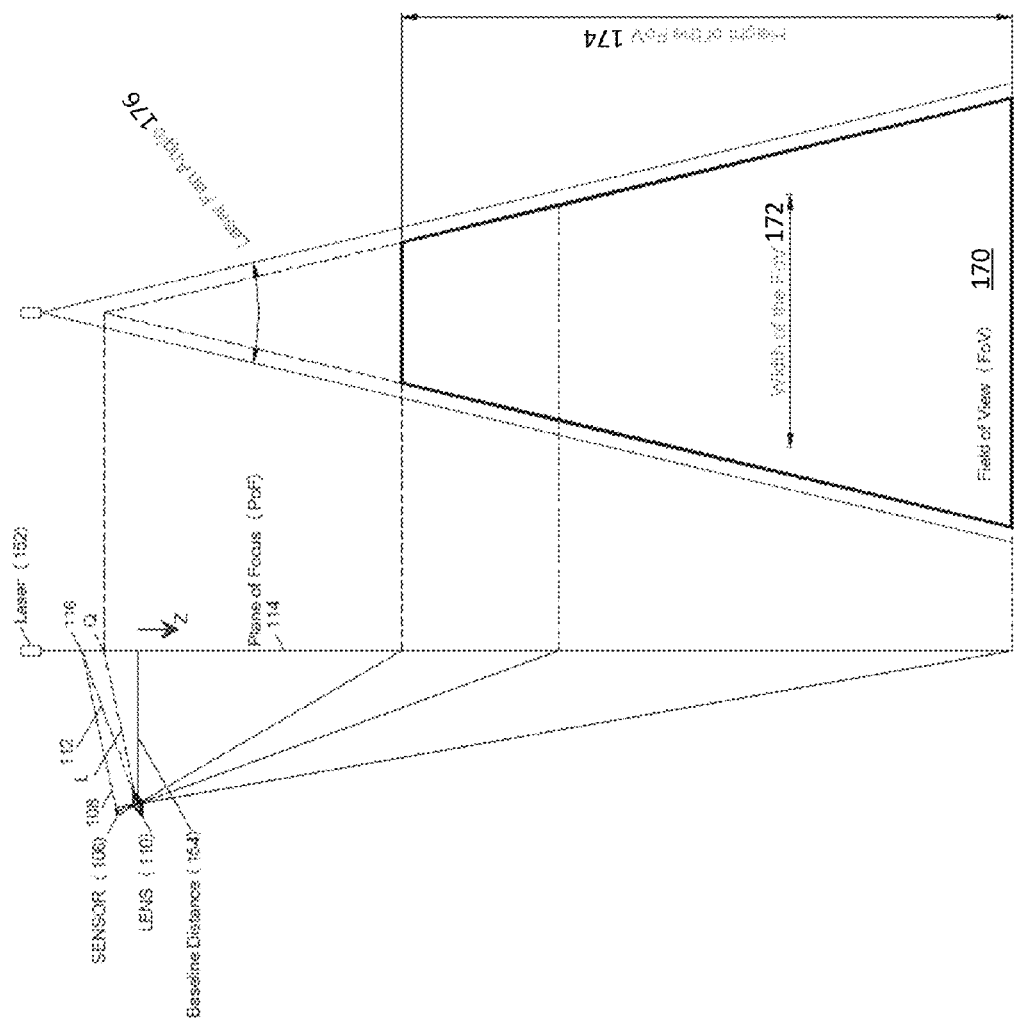
FIG. 1C illustrates the field of view of the laser-based displacement sensor in FIG. 1B, in accordance with some embodiments.

FIG. 1C illustrates the field of view of the laser-based displacement sensor shown in FIG. 1B, in accordance with some embodiments. The laser 152 projects the laser line along the PoF 114, which is rotated ninety degrees in FIG. 1C to illustrate the FOV 170. The field of view 170 is shown as a trapezoidal-shaped area which is imaged onto the sensor 106 (e.g., a rectangular sensor). The field of view 170 is defined by the width of the FOV 172, the height of the FOV 174, and the width of the laser as shown by the laser fan angle 176. The width of the FOV 172 is defined by two lines that intersect at a point Q, where point Q is defined by the intersection of line L and the PoF 114. Line L starts at the center of the lens and is parallel with sensor plane 108. The width of the FOV 172, together with the number of sensor pixels in the horizontal direction (e.g., and other factors, such as software, etc.) defines the smallest object feature that can be resolved. The height of the FOV 174, together with the number of sensor pixels in vertical direction (and/or other factors) defines the resolution of the displacement sensor's height measurement.

Figure 2:
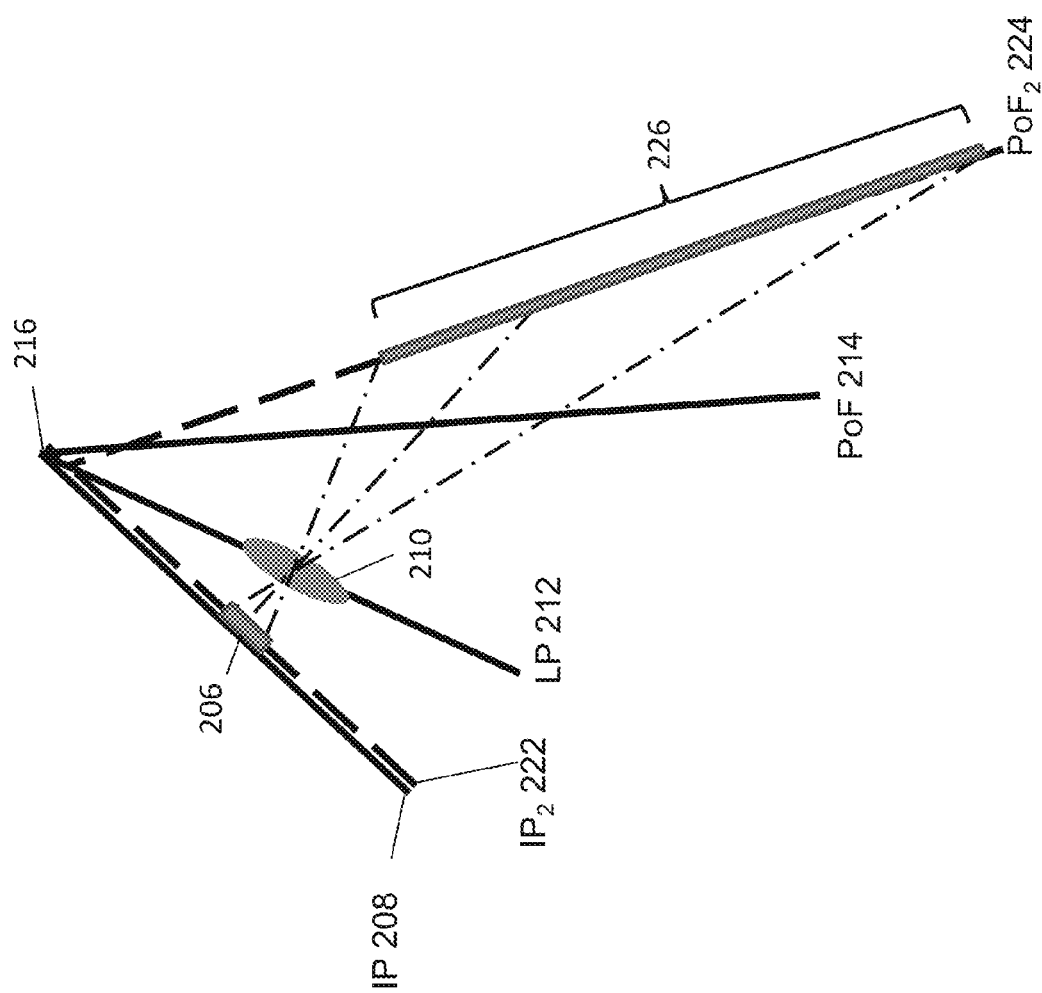
FIG. 2 is an exemplary diagram illustrating the rotation of the plane of focus caused if the image plane of the image sensor is shifted closer to the lens plane, in accordance with some embodiments.

FIG. 2 is an exemplary diagram illustrating the rotation of the plane of focus 214 caused if the image plane 208 of the image sensor 206 is shifted closer to the lens plane 212. Shifting the image plane 208 horizontally to the left to image plane location two 222 rotates the PoF 214 to PoF location two 224 such that the image sensor 206 has the FOV indicated by area 226 along the PoF two 224. However, for image sensors that use the Scheimpflug Principal for displacement sensing (e.g., measuring the displacement of an object from a base position, such as from a platform or conveyor belt), achieving a change in the FOV often requires changing the baseline (e.g., baseline 154 shown in FIG. 1B) between the laser and the imaging lens. This change in baseline often necessitates a physical change in the size of the mechanical housing for the displacement sensor, since the location of the image sensor and the laser are often fixed within the housing.

The techniques described herein can move the image sensor in a way that does not require changing the baseline between the lens and the laser. Rather than shifting the image plane towards the lens plane (e.g., as shown in FIG. 2), the image sensor 106 is translated along the image plane 108 to increase or decrease the field of view (FOV) while maintaining the same PoF. These techniques can therefore adjust the FOV such that it moves along the PoF, and therefore the baseline distance between the laser and imaging lens can remain fixed since the laser light is configured to project along the PoF. As described further below, depending on the direction of the shift of the image sensor, the FOV will either increase or decrease, allowing different configurations of the displacement sensor (e.g., near-field and far-field configurations). Such configurations can be achieved within the framework of the mechanical housing, which can eliminate the need to change the baseline of the mechanical housing, or other mechanical properties of the housing.

Figure 3A:
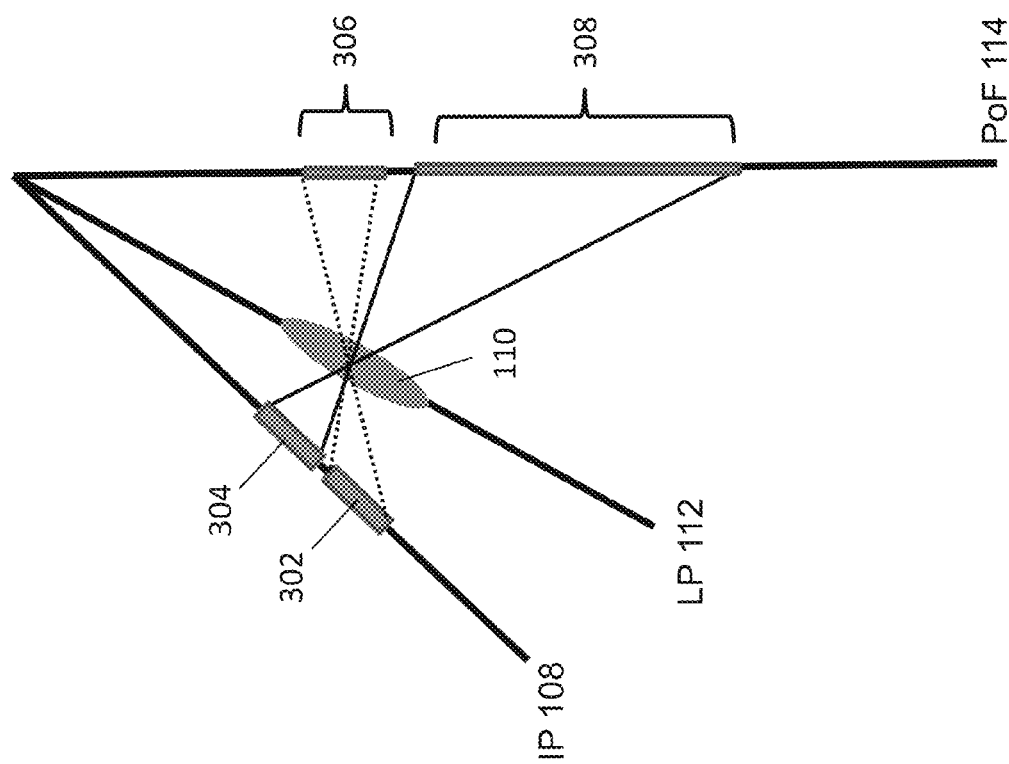
FIG. 3A is an exemplary diagram illustrating two configurations of an image sensor along an image plane and the resulting change in the FOV along the plane of focus, in accordance with some embodiments.

FIG. 3A is an exemplary diagram illustrating two configurations of the image sensor 106 along an image plane 108 and the resulting FOVs along the plane of focus, in accordance with some embodiments. When the image sensor 106 is at location 302 along the image plane 108, the image sensor 106 has a FOV 306 along PoF 114. When the image sensor 106 is moved vertically down the image plane 108 from location 302 to location 304, the FOV of the image sensor 106 moves along PoF 114 from FOV 306 to FOV 308. As shown in FIG. 3A, the FOV 306 is narrower than the FOV 308.

Figure 3B:
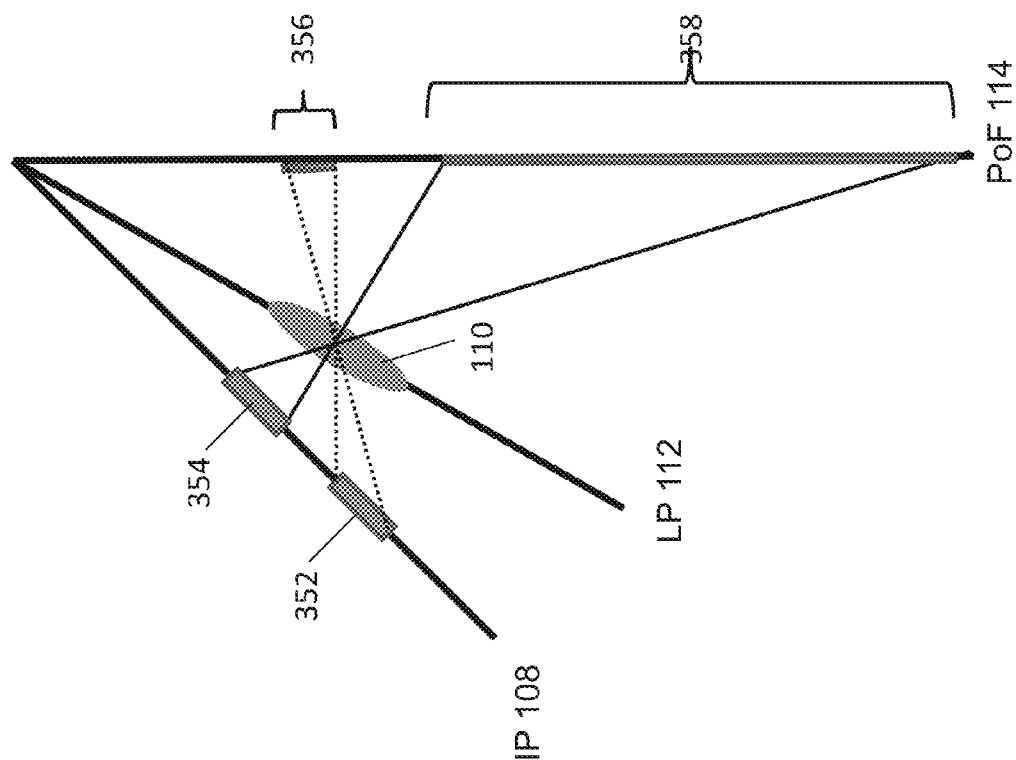
FIG. 3B is an exemplary diagram illustrating shifts in the positions of the image sensors in FIG. 3A and the resulting changes to the FOV along the plane of focus, in accordance with some embodiments.

FIG. 3B is an exemplary diagram illustrating shifts in the positions of the image sensors shown in FIG. 3A and the resulting changes to the FOVs along the plane of focus, in accordance with some embodiments. If the image sensor 106 is moved further away from the optical axis of the lens 110 (not shown) vertically down the image plane 108 from location 302 to 352, the FOV along the PoF 114 becomes smaller as indicated by FOV 356. While the optical axis is not shown, one of skill in the art can appreciate that the optical axis extends from the center of the lens 110 orthogonal to the lens plane 112 (in both directions from the lens 110). When the image sensor 106 is moved vertically up the image plane 108 from location 304 to location 354, the FOV moves along PoF 114 to FOV 358. As shown in FIG. 3B, the FOV 356 is narrower than the FOV 358. Further, comparing FIGS. 3A to 3B, FOV 356 is narrower than FOV 306, and FOV 358 is wider than FOV 308.

A narrower FOV (e.g., with a higher resolution than a wider FOV) can be used for near-field applications, while a wider FOV (e.g., with a lower resolution than a narrower FOV) can be used for far-field applications. Exemplary near-field applications include examining small objects (e.g., such as circuit board components) or other items that require high resolution. Exemplary far-field applications include examining larger objects (e.g., such as tire treads) or other items that do not require fine-grained detail.

Figure 3C:
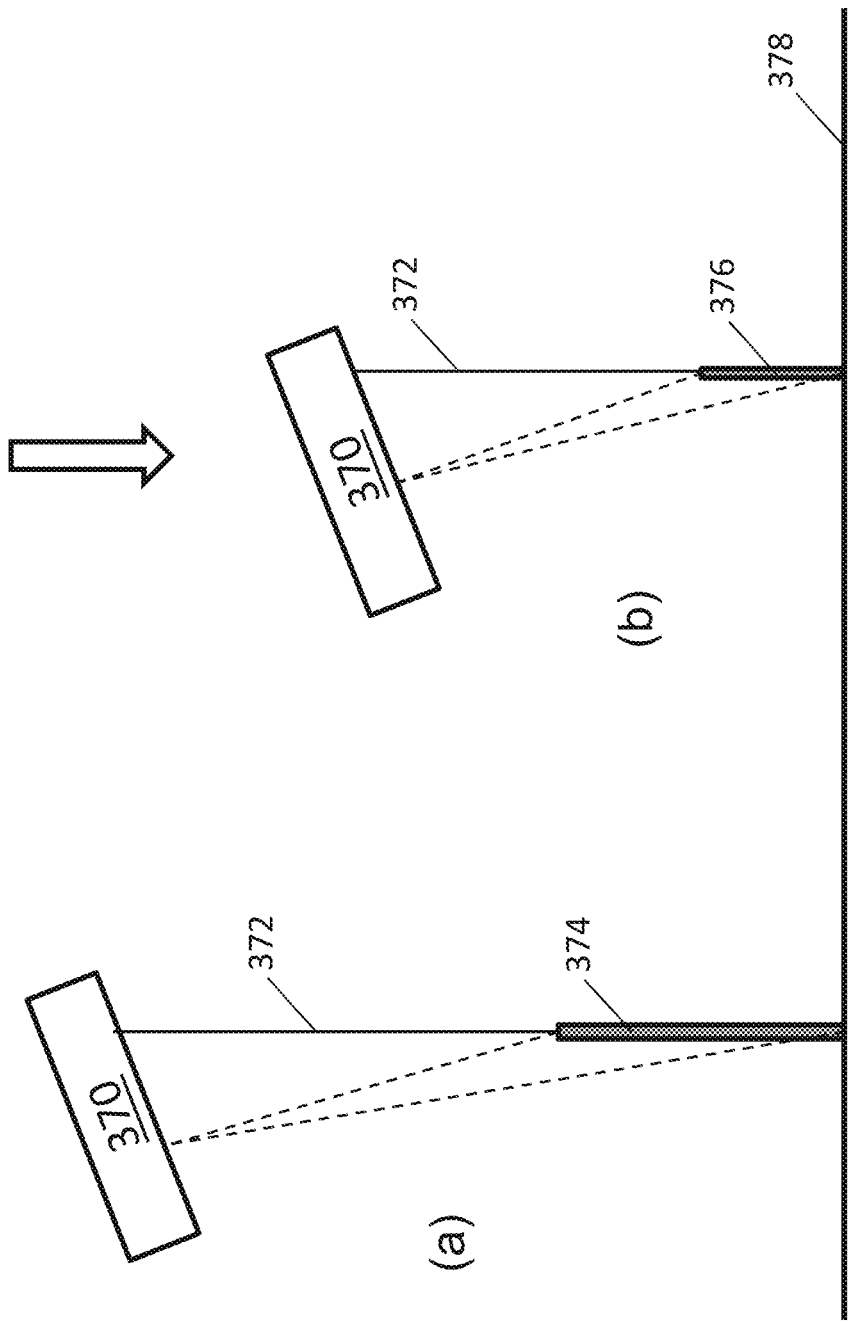
FIG. 3C is an exemplary diagram illustrating different configurations of a displacement sensor, in accordance with some embodiments.

FIG. 3C is an exemplary diagram illustrating different configurations of a displacement sensor 370, in accordance with some embodiments. The displacement sensor 370 includes a laser (not shown) that projects laser line 372 downwards onto platform 378. Configuration (a) has the image sensor (not shown) inside of the displacement sensor 370 positioned as described herein to achieve a wider FOV 374. Configuration (b) has the image sensor (not shown) inside of the displacement sensor positioned to achieve a narrower FOV 376. As shown in configuration (b), since the narrower FOV 376 is further up the laser line (e.g., and therefore further up the PoF), the displacement sensor 370 is lowered closer to the platform 378 so that the FOV 376 can measure the displacement of objects on the platform 378 (e.g., a conveyor belt used to move objects that are inspected by the displacement sensor 370).

The components of the displacement sensor can be configured to satisfy various design parameters. For example, in some embodiments the size of the lens can be enlarged to reduce vignetting (e.g., to prevent reduction in the periphery of the image captured by the image sensor). The lens can be selected so that its image circle (e.g., the cross section of the cone of light transmitted by the lens or series of lenses) can support all expected configurations of the sensor. To avoid vignetting, the lens image circle can be chosen to entirely contain the sensor. As another example, a high quality lens can be used in the displacement sensor to prevent optical aberrations, which can degrade the quality of the image. Further, the FOV adjustment of the displacement sensor can be limited to conform movements within fundamental limits in resolution of an optical system configuration in the displacement sensor. For example, if the focused field of view is far away (e.g., a wider FOV, and therefore the image sensor is further away from the object), the resolution of the acquired image may be lower than that for a closer FOV since a constraint is the image sensor. In some embodiments, different image sensors can be used for the particular application (e.g., depending on whether the FOV is close or far away from the displacement sensor).

The techniques described herein can use different optical configurations to achieve different fields of view to adapt the displacement sensor for different uses without requiring a change in the baseline between the image sensor and the laser. FIGS. 1A and 1B illustrate an exemplary embodiment that uses a motion stage to shift the image sensor to achieve different FOVs along the PoF. FIG. 4A illustrates a top perspective view of a housing 400 configurable for different printed circuit board (PCB) mounting locations, in accordance with some embodiments. The top of the housing 400 includes mounting locations 402 for mounting a lens to the housing 400, which is described in further detail with reference to FIGS. 6A-6B. The housing 400 further includes an opening 404 through which an image sensor can view a scene, which is described in further detail with respect to FIGS. 6A-7B. The housing 400 can be fixedly mounted to a displacement sensor housing that includes a laser (not shown) in the displacement sensor housing.

Figure 4B:
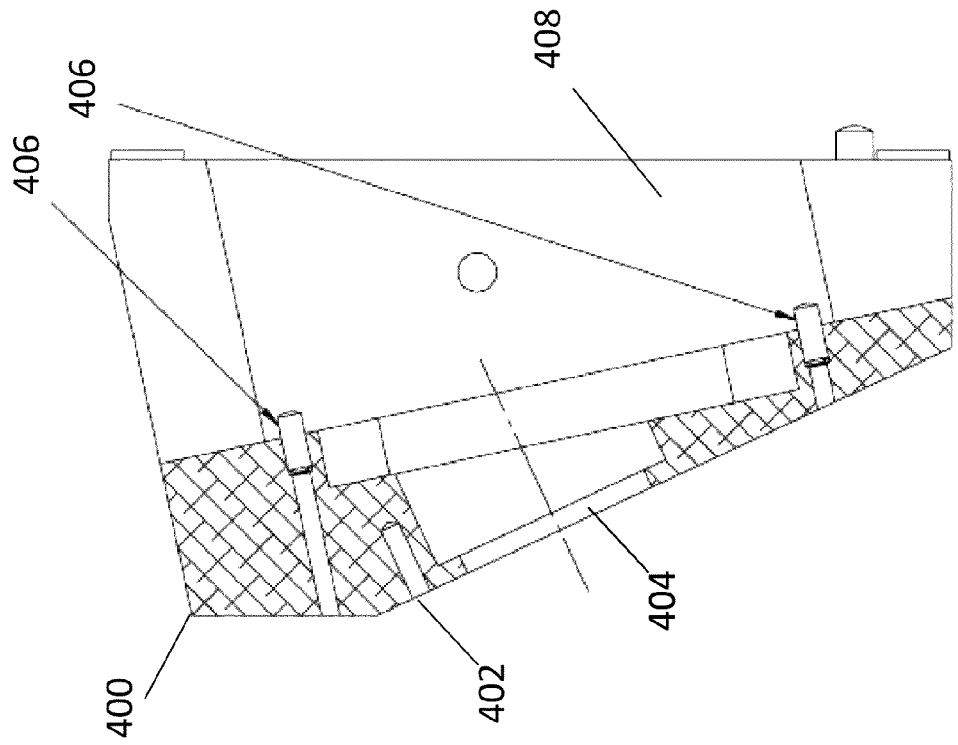
FIG. 4B illustrates a side perspective view of a housing configurable for different PCB mounting locations, in accordance with some embodiments.
Figure 4A:
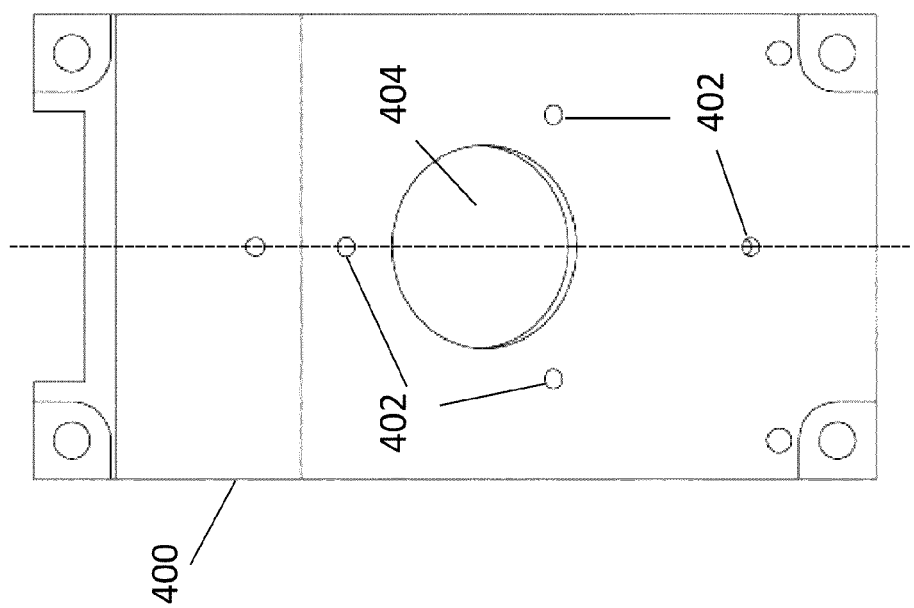
FIG. 4A illustrates a top perspective view of a housing configurable for different printed circuit board (PCB) mounting locations, in accordance with some embodiments.

FIG. 4B illustrates a side perspective view of the housing 400 of FIG. 4A, in accordance with some embodiments. FIG. 4B shows the mounting locations 402 for mounting a lens, and the opening 404. The housing 400 also includes mounting pins 406 for mounting a PCB that includes the image sensor. The mounting pins 406 protrude outwards to the cavity 408 defined by the outer perimeter of the housing 400. The mounting pins 406 can be placed in different configurations within the housing 400 to align the PCB with the image sensor at different locations to achieve a desired FOV along the PoF. For example, referring to FIG. 3C, the pins 406 can be positioned in the housing 400 used to mount the PCB at a first location to achieve the configuration shown in (a), or the pins 406 can be positioned in the housing 400 at a second location to achieve the configuration shown in (b). In some embodiments, the housing 400 is pre-configured before machining to place the pins 406 at a desired location. In some embodiments, the housing 400 has different mounting holes for the pins 406 so the pins can be adjusted to achieve different mounting configurations of the PCB.

FIG. 4C illustrates a bottom perspective view of the housing 400 also shown in FIGS. 4A and 4B, in accordance with some embodiments. FIG. 4C shows the opening 404, and the mounting pins 406 shown in FIGS. 4A and 4B. FIG. 4C also shows screw holes 410 for using screws to secure the PCB to the housing 400.

Figures 5A, 5B:
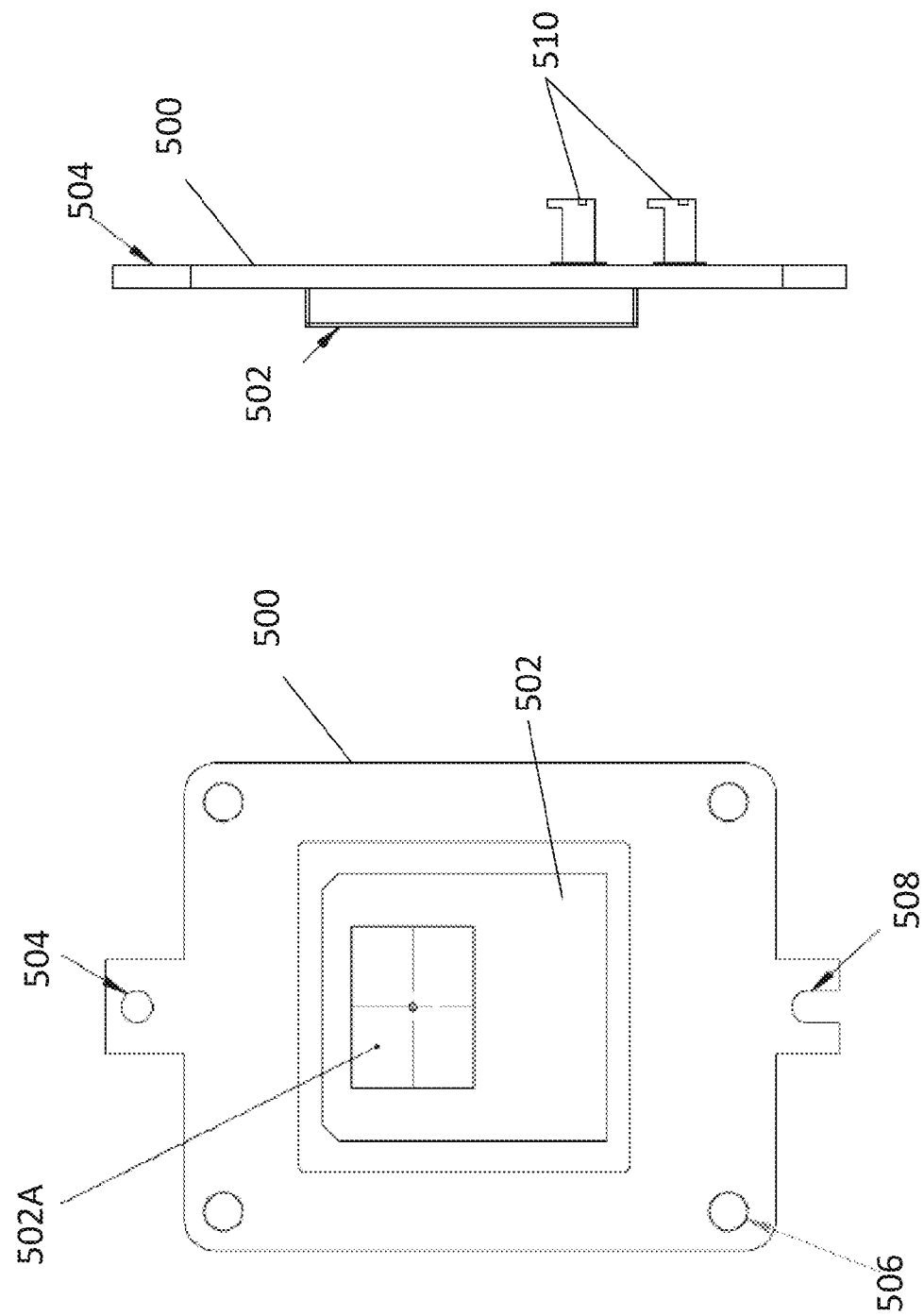
FIG. 5A illustrates a top perspective view of an image plane sensor mounted on a PCB, in accordance with some embodiments.
FIG. 5B illustrates a top perspective view of an image plane sensor mounted on a PCB, in accordance with some embodiments.

FIG. 5A illustrates a top perspective view of an image plane sensor 502 mounted on a PCB 500, in accordance with some embodiments. The image sensor 502 includes active area 502A. The PCB 500 includes a slot 508 through the circuit board for a first locating pin. The PCB 500 includes four holes 506 through the PCB for mounting screws to mount the PCB to the housing (e.g., as described in further detail below with respect to FIGS. 6A and 6B). The PCB 500 includes a hole 504 through the circuit board for a second locating pin. FIG. 5B illustrates a side perspective view of the image plane sensor 502 and PCB 500 from FIG. 5A, in accordance with some embodiments. The connectors 510 are used to connect the image sensor 502 to the image processing device (not shown).

One of skill in the art can appreciate that different configurations other than those shown in exemplary FIGS. 4A-5B can be used to achieve the desired effect of being able to mount the PCB 500 within the housing 400 at different locations without departing from the spirit of the invention. For example, only one locator pin may be used and therefore only one corresponding slot in the PCB. Similarly, any other number of locator pins may be used, or the locator pins may help align the outside of the PCB without protruding through the PCB. Further, in some embodiments other alignment mechanisms besides locator pins can be used, such as just the screw holes 506, other fastening devices, and/or the like.

Figure 6A:
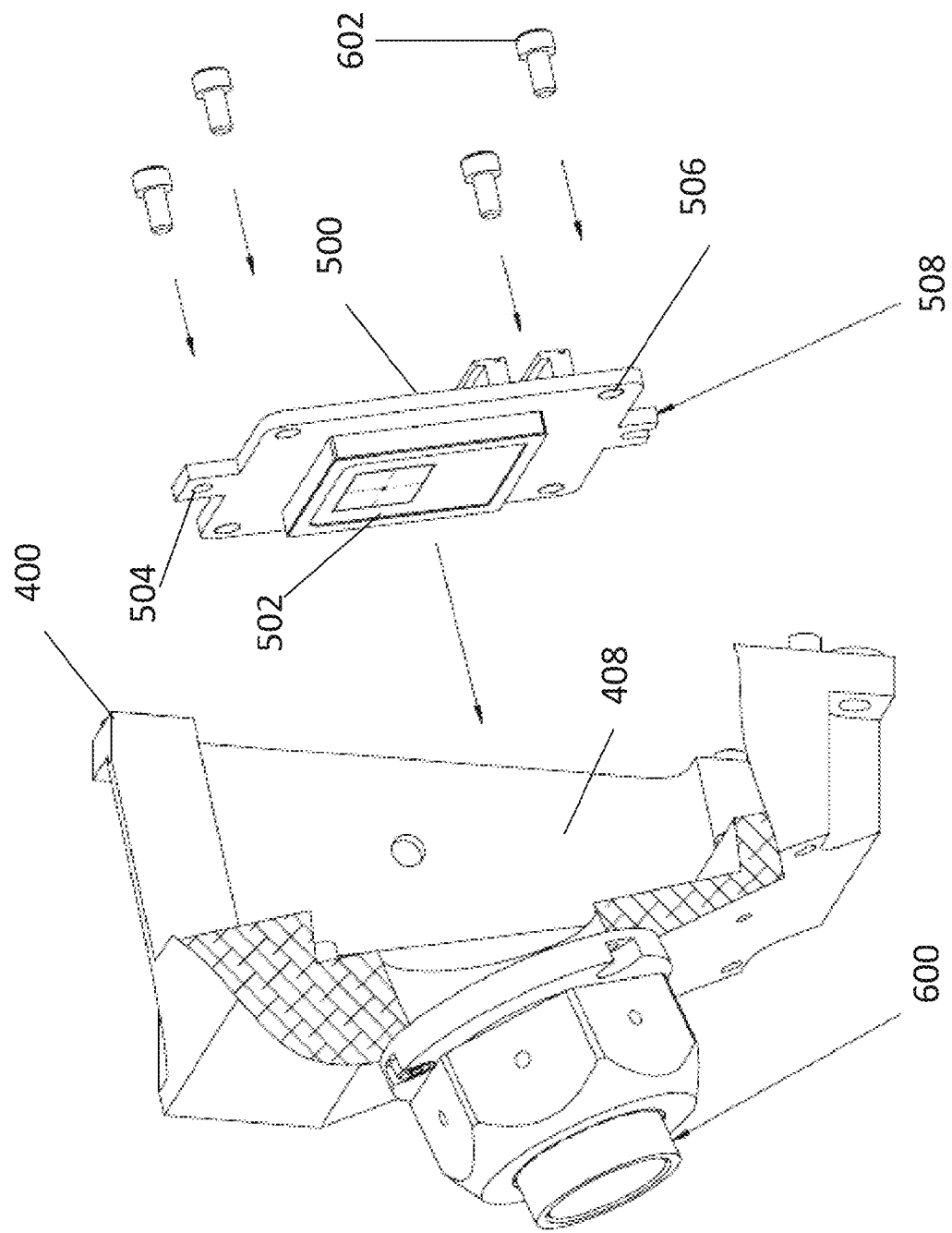
FIG. 6A illustrates a side perspective view of a lens mounted on the housing and how a PCB with an image plane sensor is inserted into the cavity of the housing, in accordance with some embodiments.
Figure 6B:
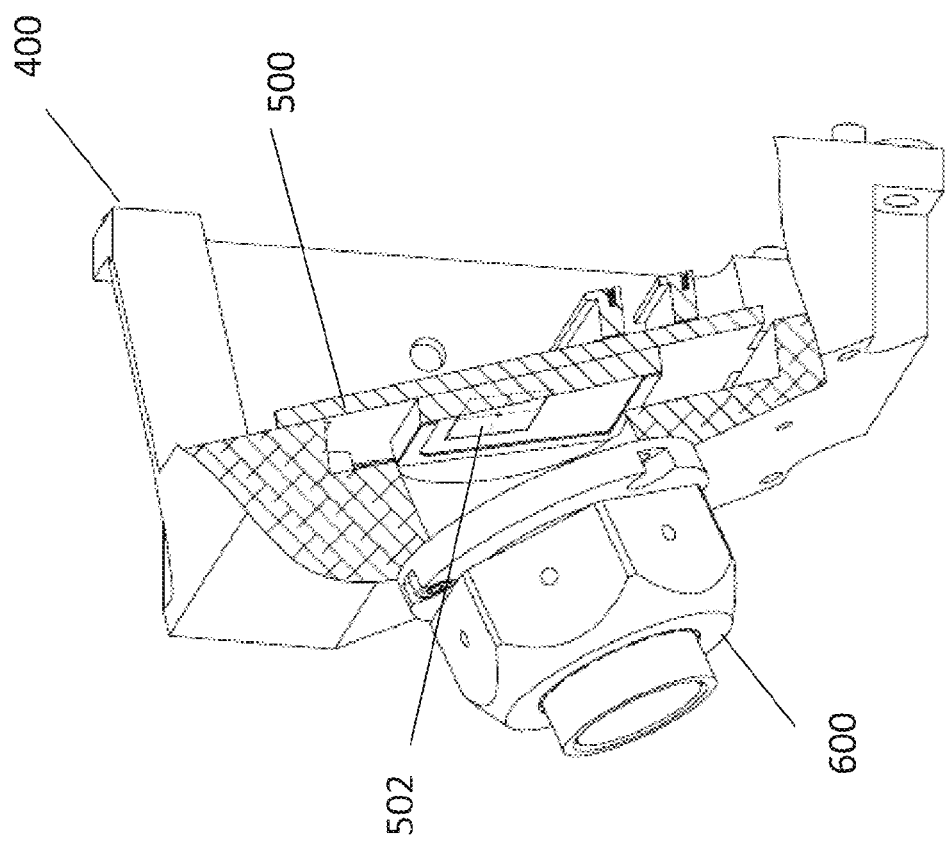
FIG. 6B illustrates a side perspective view of the lens and the PCB with the image plane sensor mounted on the housing, in accordance with some embodiments.

FIG. 6A illustrates a side perspective view of a lens structure 600 mounted on the housing 400, and how the PCB 500 with the image plane sensor 502 is inserted into the cavity 408 of the housing 400, in accordance with some embodiments. The PCB 500 is inserted into the cavity 408 (using the mounting pins 406 to align the PCB to the body 400) and fastened to the housing 400 using the screws 602 that pass through a corresponding hole 506 in the PCB 500. FIG. 6B illustrates a side perspective view of the lens structure 600 and the PCB 500 with the image plane sensor 502 mounted on the housing, in accordance with some embodiments. The image sensor 502 is positioned within the housing using the locator pins to align the image sensor 502 with respect to the lens structure 600 to achieve a desired FOV, as described herein.

The PCB 500 can be mounted in different locations within the housing to achieve different FOVs. FIG. 7A illustrates a side perspective view of the lens structure 600 and the PCB 500 with the image plane sensor 502 mounted within the housing 400 at a nominal position, in accordance with some embodiments. The center location of the active area 502a of image sensor 502 is on the optical axis 702 of the lens structure 600. Lens structure 600 includes air gaps 600a and 600b. The lens structure 600 includes a filter 600c configured to block visible light other than the laser wavelength. The lens structure 600 also includes the imager lens 600d.

Figure 7B:
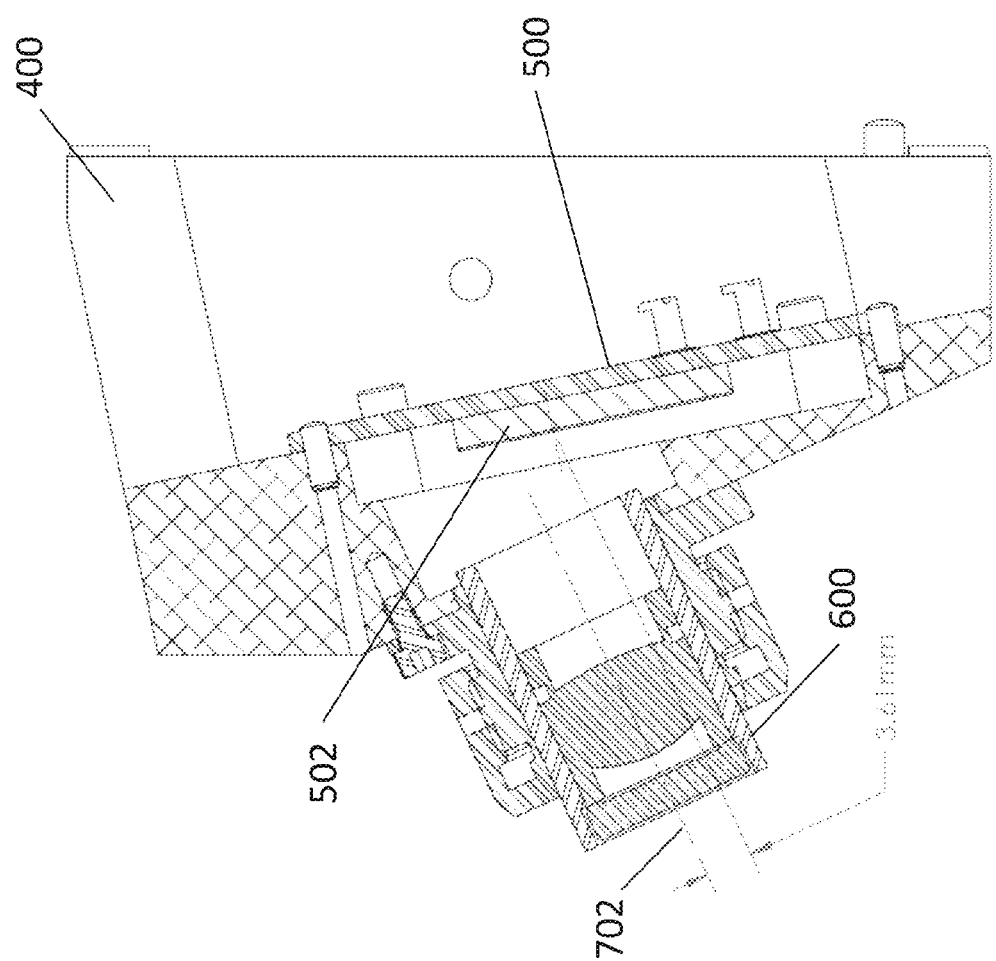
FIG. 7B illustrates a side perspective view of the lens and the PCB with the image plane sensor mounted within the housing at a far field position, in accordance with some embodiments.

FIG. 7B illustrates a side perspective view of the lens structure 600 and the PCB 500 with the image plane sensor 502 mounted within the housing 400 at a far field position, in accordance with some embodiments. As shown in the example of FIG. 7B, the center location of the active area 502A of image sensor 502 is offset from the optical axis 702 of the lens structure 600 by 3.61 mm. For example, 3.61 mm can represent a shift of approximately half of the image sensor height (e.g., so one side of sensor will be on the optical axis of the lens, such as the horizontal side of the sensor).

Figure 7C:
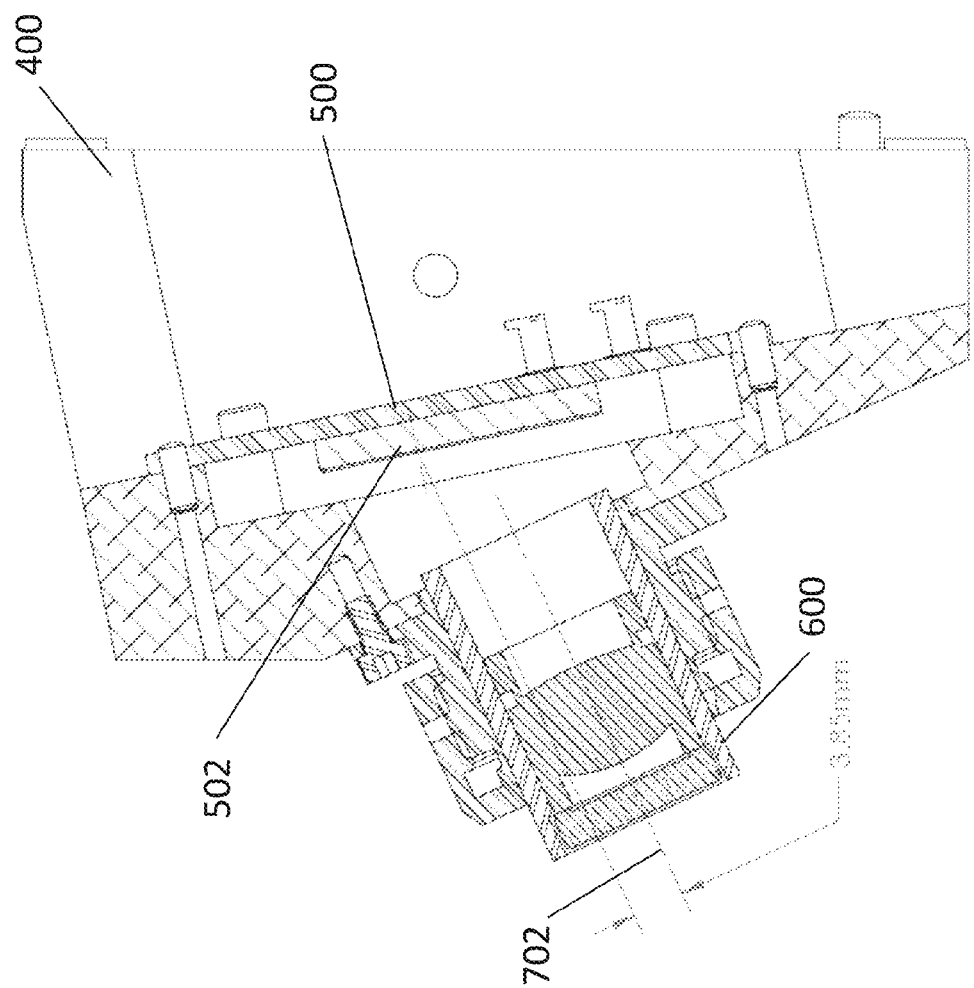
FIG. 7C illustrates a side perspective view of the lens and the PCB with the image plane sensor mounted within the housing at a near field position, in accordance with some embodiments.

FIG. 7C illustrates a side perspective view of the lens structure 600 and the PCB 500 with the image plane sensor 502 mounted within the housing 400 at a near field position, in accordance with some embodiments. As shown in the example of FIG. 7C, the center location of the active area 502A of image sensor 502 is offset from the optical axis 702 of the lens structure 600 by 3.85 mm from the optical axis 702 in the opposite direction than in FIG. 7C. Similar to FIG. 7B, 3.85 mm can represent a shift of approximately half of the image sensor height (e.g., so the other side of sensor will be on the optical axis of the lens, compared to FIG. 7B).

In some examples, the thickness of the laser line is changed between the different configurations. In some embodiments, the displacement sensor is configured so that the laser is removable to allow use of different lasers to project laser lines with different thicknesses based on the image sensor's configured FOV. For example, if the displacement sensor is being used for a near-field application, a laser line with a first thickness may be necessary, whereas for a far-field application, a thicker laser line is desirable. While the laser can be removable, the baseline between the laser and the lens can be pre-configured to not change. The length of the laser line can be configured so that it is larger than the width of the FOV (e.g., such that the fan angle is sufficiently large), which may not require changing the laser in this sensor.

In some embodiments, the laser can be focused or configured such that the beam is tightest for the particular FOV. For example, some lensed laser widths may vary across the FOV, so the position where the beam is thinnest corresponds to the laser's best focus, while the laser's line gets wider as it gets more out of focus (e.g., further away from the best focus position). The laser can be configured or selected so that the laser's best focus aligns with the FOV (e.g., so where the beam is thinnest aligns with the FOV).

In some embodiments, the displacement sensor is configured so that the image sensor is removable (e.g., different PCBs can be configured into the displacement sensor housing). For example, if the displacement sensor is being used for a near-field application, an image sensor with high resolution may be used to inspect small parts/features, whereas for a far-field application, less resolution is necessary.

In some embodiments, one or more of the modules (e.g., modules used to adjust the position of the image sensor) can be implemented in software using memory. The memory can be a non-transitory computer readable medium, flash memory, a magnetic disk drive, an optical drive, a programmable read-only memory (PROM), a read-only memory (ROM), or any other memory or combination of memories. The software can run on a processor capable of executing computer instructions or computer code. The processor might also be implemented in hardware using an application specific integrated circuit (ASIC), programmable logic array (PLA), digital signal processor (DSP), field programmable gate array (FPGA), or any other integrated circuit.

Method steps can be performed by one or more processors executing a computer program to perform functions of the invention by operating on input data and/or generating output data. One or more of the modules can be implemented in hardware using an ASIC (application-specific integrated circuit), PLA (programmable logic array), DSP (digital signal processor), FPGA (field programmable gate array), or other integrated circuit. In some embodiments, two or more modules can be implemented on the same integrated circuit, such as ASIC, PLA, DSP, or FPGA, thereby forming a system on chip. Subroutines can refer to portions of the computer program and/or the processor/special circuitry that implement one or more functions.

In some embodiments, the computing device can include user equipment. The user equipment can communicate with one or more radio access networks and with wired communication networks. The user equipment can be a cellular phone. The user equipment can also be a smart phone providing services such as word processing, web browsing, gaming, e-book capabilities, an operating system, and a full keyboard. The user equipment can also be a tablet computer providing network access and most of the services provided by a smart phone. The user equipment operates using an operating system such as Symbian OS, iPhone OS, RIM's Blackberry, Windows Mobile, Linux, HP WebOS, and Android. The screen might be a touch screen that is used to input data to the mobile device, in which case the screen can be used instead of the full keyboard. The user equipment can also keep global positioning coordinates, profile information, or other location information.

The computing device can also include a server. The server can operate using an operating system (OS) software. In some embodiments, the OS software is based on a Linux software kernel and runs specific applications in the server such as monitoring tasks and providing protocol stacks. The OS software allows server resources to be allocated separately for control and data paths. For example, certain packet accelerator cards and packet services cards are dedicated to performing routing or security control functions, while other packet accelerator cards/packet services cards are dedicated to processing user session traffic. As network requirements change, hardware resources can be dynamically deployed to meet the requirements in some embodiments.

The above-described techniques can be implemented in digital electronic circuitry, or in computer hardware, firmware, software, or in combinations of them. The implementation can be as a computer program product, e.g., a computer program tangibly embodied in a machine-readable storage device, for execution by, or to control the operation of, a data processing apparatus, e.g., a programmable processor, a computer, and/or multiple computers. A computer program can be written in any form of computer or programming language, including source code, compiled code, interpreted code and/or machine code, and the computer program can be deployed in any form, including as a stand-alone program or as a subroutine, element, or other unit suitable for use in a computing environment. A computer program can be deployed to be executed on one computer or on multiple computers at one or more sites.

Processors suitable for the execution of a computer program include, by way of example, both general and special purpose microprocessors, digital signal processors, and any one or more processors of any kind of digital computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. A computer can be operatively coupled to external equipment, for example factory automation or logistics equipment, or to a communications network, for example a factory automation or logistics network, in order to receive instructions and/or data from the equipment or network and/or to transfer instructions and/or data to the equipment or network. Computer-readable storage devices suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

We claim:

1. A displacement sensor for determining characteristics of an object, comprising:
    an optical lens disposed on a lens plane;
    an image sensor, disposed on an image plane that is not parallel to the lens plane, configured to capture an image of an object along a plane of focus that is not parallel to the image plane
    a light source for illuminating the object by the displacement sensor, wherein the light source is:
    spaced from the lens at a fixed distance; and
    configured to project light along the plane of focus of the image sensor;
    wherein the image sensor is configured to be placed at:
        a first location along the image plane to obtain a first field of view along the plane of focus, and
        a second location along the image plane to obtain a second field of view along the plane of focus that is wider than the first field of view.

2. The displacement sensor of claim 1, wherein the image sensor is configured to be placed at the first position to obtain an image of a small object or a feature of the small object with a first level of detail, and wherein the image sensor is configured to be placed at the second position to obtain an image of a large object or large feature of an object with a second level of detail, wherein the first level of detail is higher than the second level of detail.

3. The displacement sensor of claim 1, further comprising:
    a motion stage configured to mount the image sensor, disposed on a plane parallel to the image plane, configured to move the image sensor on the image plane; and
    a controller configured to move the motion stage to position the image sensor at the first location or the second location.

4. The displacement sensor of claim 1, further comprising one or more locator pins, wherein the one or more locator pins can be provided in a first locator pin configuration to align the one or more locator pins with the image sensor placed at the first location, and wherein the one or more locator pins can be provided in a second locator pin configuration to align the one or more locator pins with the image sensor placed at the second location.

5. The displacement sensor of claim 1, wherein the image sensor is at a third location in the displacement sensor to provide a third field of view along the plane of focus, wherein the third field of view is wider than the second field of view.

6. The displacement sensor of claim 1, wherein the image sensor is configured to view the object through the lens using the Scheimpflug principle to provide the first field of view and the second field of view by shifting the image sensor along the image plane not parallel to the plane of focus.

7. The displacement sensor of claim 1, wherein the light source comprises a laser for illuminating the object configured to project a line of light along the plane of focus of the image sensor.

8. The displacement sensor of claim 7, wherein:
when the image sensor is placed at the first location, the laser is configured to project a first line of light with a first thickness to illuminate the object for inspection; and
when the image sensor is placed at the second location, the laser is configured to project a second line of light with a second thickness greater than the first thickness to illuminate the object for inspection.

9. The displacement sensor of claim 8, wherein the laser is removably provided in the displacement sensor.

10. The displacement sensor of claim 1, wherein the image sensor is removably provided in the displacement sensor.

11. A displacement sensor for determining characteristics of an object, comprising:
an optical lens disposed on a lens plane;
an image sensor, disposed on an image plane that is not parallel to the lens plane, configured to capture an image of an object along a plane of focus that is not parallel to the image plane
a light source for illuminating the object by the displacement sensor, wherein the light source is:
spaced from the lens at a fixed distance; and
configured to project light along the plane of focus of the image sensor;
wherein the image sensor is configured to be placed at:
a first location along the image plane to obtain a first field of view along the plane of focus; and
a second location along the image plane to obtain a second field of view along the plane of focus that is wider than the first field of view.

12. The displacement sensor of claim 11, further comprising:
a motion stage configured to mount the image sensor, disposed on a plane parallel to the image plane, configured to move the image sensor on the image plane; and
a controller configured to move the motion stage to position the image sensor at the first location or the second location.

13. The displacement sensor of claim 11, further comprising one or more locator pins, wherein the one or more locator pins can be provided in a first locator pin configuration to align the one or more locator pins with the image sensor placed at the first location, and wherein the one or more locator pins can be provided in a second locator pin configuration to align the one or more locator pins with the image sensor placed at the second location.

14. The displacement sensor of claim 11, wherein the image sensor is at a third location in the displacement sensor to provide a third field of view along the plane of focus, wherein the third field of view is wider than the second field of view.

15. A method of manufacturing a displacement sensor, comprising:
mounting an optical lens disposed on a lens plane to a displacement sensor housing;
mounting an image sensor, disposed on an image plane not parallel to the lens plane, to the displacement sensor housing, wherein the image sensor is configured to capture an image of an object along a plane of focus that is not parallel to the image plane of the image sensor, and wherein the displacement sensor is mounted in one of a plurality of configurations comprising:
a first configuration in which the image sensor is at a first location along the image plane of the image sensor to provide a first field of view along the plane of focus; and
a second configuration in which the image sensor is at a second location along the image plane of the image sensor to provide a second field of view along the plane of focus that is wider than the first field of view,
mounting a light source for illuminating the object by the displacement sensor on the displacement sensor housing, wherein the light source is:
spaced from the lens at a fixed distance; and
configured to project light along the plane of focus of the image sensor.

16. The method of claim 15, further comprising mounting the image sensor on a motion stage configured to move along an axis defined within the image plane.

17. The method of claim 15, further comprising installing one or more locator pins in the displacement sensor housing in one of a plurality of locator pin configurations comprising:
a first locator pin configuration in which the one or more locator pins are aligned to the image sensor in the first location; and
a second locator pin configuration in which the one or more locator pins are aligned to the image sensor in the second location.

18. The method of claim 17, wherein the locator pins are machined in the one of the plurality of locator pin configurations.

19. The method of claim 15, wherein the light source comprises a laser that is removably mounted to the displacement sensor housing to allow for use of a first laser to project a first line of light and a second laser to project a second line of light.

20. The method of claim 15, wherein the image sensor is removably mounted to the displacement sensor housing to allow for use of a first image sensor for the first configuration and a second image sensor for the second configuration.

* * * * *